United States Patent
Park et al.

(10) Patent No.: US 9,011,929 B2
(45) Date of Patent: Apr. 21, 2015

(54) COMPOSITION FOR INDUCING TISSUE REGENERATION BY ACTIVATING PLATELET-RICH PLASMA (PRP)

(75) Inventors: Hyun-Shin Park, Seoul (KR); Ji-Chul Yu, Seoul (KR); Ju-Hee Park, Seoul (KR); Jang-Hoon Kim, Seoul (KR); Hun Kim, Seoul (KR); Sae-Bom Lee, Seoul (KR); Jae-Deog Jang, Seoul (KR); Cheong-Ho Jang, Seoul (KR)

(73) Assignee: Sewon Cellontech Co., Ltd., Seoul (KR)

( * ) Notice: Subject to any disclaimer, the term of this patent is extended or adjusted under 35 U.S.C. 154(b) by 400 days.

(21) Appl. No.: 13/502,116

(22) PCT Filed: Nov. 17, 2009

(86) PCT No.: PCT/KR2009/006745
§ 371 (c)(1),
(2), (4) Date: Apr. 13, 2012

(87) PCT Pub. No.: WO2011/049263
PCT Pub. Date: Apr. 28, 2011

(65) Prior Publication Data
US 2012/0201897 A1    Aug. 9, 2012

(30) Foreign Application Priority Data
Oct. 23, 2009  (KR) .................. 10-2009-0101387

(51) Int. Cl.
| | | |
|---|---|---|
| *A61K 35/16* | (2006.01) | |
| *A61K 38/39* | (2006.01) | |
| *A61L 27/36* | (2006.01) | |
| *A61L 27/24* | (2006.01) | |
| *A61L 27/38* | (2006.01) | |

(52) U.S. Cl.
CPC ............ *A61L 27/3616* (2013.01); *A61K 35/16* (2013.01); *A61K 38/39* (2013.01); *A61L 27/24* (2013.01); *A61L 27/38* (2013.01)

(58) Field of Classification Search
None
See application file for complete search history.

(56) References Cited

U.S. PATENT DOCUMENTS

| | | | | |
|---|---|---|---|---|
| 6,280,727 | B1 * | 8/2001 | Prior et al. ................. | 424/94.63 |
| 6,322,785 | B1 * | 11/2001 | Landesberg et al. ....... | 424/93.72 |
| 2007/0037737 | A1 | 2/2007 | Hoemann et al. | |
| 2008/0166421 | A1 | 7/2008 | Buhr et al. | |

FOREIGN PATENT DOCUMENTS

| | | |
|---|---|---|
| KR | 10-2002-0012170 A | 2/2002 |
| WO | 2009016451 A2 | 2/2009 |

OTHER PUBLICATIONS

Fufa et al, J Oral Maxillofac Surg, 2008, vol. 66, p. 684-690.*

* cited by examiner

*Primary Examiner* — Allison Fox
(74) *Attorney, Agent, or Firm* — Novick, Kim & Lee, PLLC; Jae Youn Kim

(57) ABSTRACT

The present invention relates to a composition for cartilaginous tissue repair and to a production method therefor. The present invention comprises the steps of: (a) dissolving freeze-dried fibrinogen in an aprotinin solution; (b) dissolving freeze-dried thrombin in a stabilizing solution; (c) mixing an enriched collagen solution with thrombin and the stabilizing solution; and installing the fibrinogen solution (a) to one side of a dual kit and the solution (c) containing the collagen to the other side, and then mixing and injecting into damaged cartilaginous tissue. In the present invention, which is constituted as described above, biomaterials such as collagen and fibrin are mixed so as to allow damaged cartilaginous tissue to be repaired to a state allowing transplantation onto the tissue, and efficient regeneration is induced, thereby making it possible to reduce surgery-related stress on people and animals while inducing relatively rapid and efficient cartilage repair and regeneration.

2 Claims, 3 Drawing Sheets

COMPOSITION FOR INDUCING TISSUE REGENERATION BY ACTIVATING PLATELET-RICH PLASMA (PRP)

TECHNICAL FIELD

The present invention relates to a composition for inducing tissue regeneration by activating platelet rich plasma (PRP) with a calcium chloride solution and type I collagen, and a method of manufacturing the same. More particularly, in the present invention, the composition may have a gel-type of formation containing PRP, and may be transplanted to any lesion in need of tissue regeneration in cases such as bone defect treatment and wound healing, and accordingly, PRP may be activated to induce a growth factor which is useful for tissue regeneration from PRP gel to conveniently and quickly achieve effective tissue regeneration. Accordingly, the method is very useful in highly enhancing the credibility of applying PRP to lesions and presenting a good image to consumers.

BACKGROUND ART

As generally known, platelet rich plasma (PRP) is an autologous material separated from whole blood through density gradient centrifugation, and is an inactive substance that includes a large amount of platelets concentrated with respect to a small amount of plasma, and contains leukocytes in a high-concentration.

Inactivated platelets within a blood vessel maintain a round shape while circulating through the blood vessel. It is known that the platelets have a life span of about 10 days, and are present in an amount of about $2{\sim}10^8$ with respect to 1 mL of the blood.

Platelets within PRP are activated through substances included within a blood vessel, and then release growth factors and various active substances. The activating substances include collagen, thrombin, adenosine diphosphate (ADP) and epinephrine. Especially, collagen and thrombin are known as strong agonists. It is known that collagen induces the activation of the platelets through the adhesion of its specific sequence onto the platelets as shown in FIG. 1.

When activating factors activate the platelets, the platelets release growth factors due to degranulation of their alpha granules. The factors perform an important role in initial wound healing. Herein, the released growth factors include platelet derived growth factor (PDGF-AB), transforming growth factor-b1 (TGF-b1), vascular endothelial growth factor (VEGF), epidermal growth factor (EGF), insulin-like growth factor (IGF) and the like. Also, PRP releases cytokine, etc. under in vitro condition, thereby synthesizing DNA of fibroblasts. This increases the production of collagen, and thus allows a collagen structure to be organized.

However, in the application of PRP in a liquid state, it is difficult to inject the PRP into a wound, and there exists a loss of surrounding tissues. Thus, it is required to develop clotting gelation accompanied by physical properties. For the gelation, research on the use of thrombin has been recently mainly conducted. However, there is a report that in the use of thrombin (mainly bovine-derived), that is an animal-derived protein, an immune reaction such as lupus was observed. In other words, thrombin is known as a factor having clinical problems related to an antibody. Thrombin is the most potent component as a platelet activator. However, when thrombin is used, antibodies to thrombin, prothrombin, factor V, and cardiolipin are required. Also, through animal research, it was found that there are clinical problems such as after-operation bleeding, and an autoimmune syndrome. Although these problems rarely occur, they cannot be neglected in development. The use of thrombin may cause the spread of damaged wound, abnormal strength of gel or the like.

Furthermore, due to high contractility of a thrombin-activating gel, there exists a difficulty in the surgical procedure for filling a wound space. Thus, the importance of a replacement material for thrombin has been recognized.

Collagen is a rigid fibrous protein, and is a main protein component of a mammalian connective tissue. It makes up 30% or more of total proteins. The collagen provides shape, strength and flexibility to the tissue, and has various functions such as tissue scaffolding, cell adhesion, cell migration, blood vessel production, tissue morphogenesis, tissue repair, and the like. Collagen, as a strong agonist of platelets, activates the platelets, and causes platelet aggregation. Fibrillar collagen more strongly induces platelet aggregation and supports greater platelet adhesion than a soluble collagen. Although the reason for such a difference has not been clearly proven, it is assumed that there is a possibility that the fibrillar collagen binds to a molecule increasing the action of activated platelets.

Type I collagen makes up a majority of mammalian connective tissue. Also, as a natural scaffold, it is most actively researched in the fields of regenerative medicine and tissue engineering. Due to these advantages of type I collagen, the type I collagen performs a role of activating platelets by replacing thrombin, and maintaining the shape.

However, there has been no composition for inducing tissue regeneration by activating PRP with a calcium chloride solution and the type I collagen. In other words, there has been no substitute for thrombin. Thus, only the thrombin (mainly bovine-derived), that is, an animal-derived protein, has been used despite its many problems.

DISCLOSURE

Technical Problem

Therefore, the present invention has been made in view of the above-mentioned problems, and provides a composition for inducing tissue regeneration by activating platelet rich plasma (PRP), and a method of manufacturing the same. The present invention achieves the following objects. First, in order to improve an immune reaction and clinical problems, type I collagen is used, in which the immune reaction and the clinical problems are caused when platelet rich plasma (PRP) is used together with an animal-derived protein, that is, thrombin (mainly bovine-derived). Second, for bone defect treatment or wound healing, a small amount of whole blood is collected, and PRP is separated from the whole blood and is injected in mixture with type I collagen. In other words, platelet rich plasma (PRP) as an autologous material and atelocollagen causing few immune reactions are used so as to eliminate clinical rejection. Third, PRP is conveniently and quickly separated on site for a surgical procedure, and is injected in a mixture with a calcium chloride solution and type I collagen, so that effective tissue regeneration can be achieved for severely injured patients or patients undergoing repetitive operations. Fourth, when the PRP collected according to the present invention is applied to a region requiring tissue-regeneration in a mixture with a calcium chloride solution and type I collagen, type I collagen activates PRP, inducing growth factors useful for tissue regeneration from the PRP gel. This is effective to conveniently and quickly achieve tissue regeneration. Especially, fifth, the clotting of type I collagen as an agonist with PRP can release a similar or larger amount of growth factors according to the kinds of the growth factors, than that in the clotting of thrombin as an agonist with PRP. This induces more effective tissue regeneration. Furthermore, sixth, the PRP collected according to the present invention is injected in a mixture with a calcium chloride solution and type I collagen into all regions requiring bone defect treatment or wound healing, thereby achieving effective tissue regeneration. Finally, seventh, as a result, the invention highly enhances the credibility of applying PRP to lesions and presents a good image to consumers.

Technical Solution

In accordance with an aspect of the present invention, there is provided a method of manufacturing a composition for inducing tissue regeneration by activating platelet rich plasma (PRP), the method including the steps of: separating PRP from whole blood; mixing the PRP with a calcium chloride solution; and mixing a mixture of the PRP and the calcium chloride solution with type I collagen.

In accordance with another aspect of the present invention, there is provided a composition for inducing tissue regeneration by activating PRP, which is manufactured by the method.

Advantageous Effects

As described in detail hereinabove, in the present invention, in order to improve an immune reaction and clinical problems, type I collagen is used, in which the immune reaction and the clinical problems are caused when platelet rich plasma (PRP) is used together with an animal-derived protein, that is, thrombin (mainly bovine-derived).

In the above described technical configuration of the present invention, for bone defect treatment or wound healing, a small amount of whole blood is collected, and platelet rich plasma (PRP) is separated from the whole blood and is injected in mixture with type I collagen. In other words, PRP as an autologous material and atelocollagen causing few immune reactions are used so as to eliminate clinical rejection.

Also, in the present invention, PRP is conveniently and quickly separated on site for a surgical procedure, and is injected in a mixture with a calcium chloride solution and type I collagen, so that effective tissue regeneration can be achieved for severely injured patients or patients undergoing repetitive operations.

Also, when the PRP collected according to the present invention is applied to a region requiring tissue-regeneration in a mixture with a calcium chloride solution and type I collagen, type I collagen activates the PRP, inducing growth factors useful for tissue regeneration from PRP gel. This is effective to conveniently and quickly achieve the tissue regeneration.

Especially, in the present invention, the clotting of type I collagen as an agonist with PRP can release a similar or larger amount of growth factors according to the kinds of the growth factors, than that in the clotting of thrombin as an agonist with PRP. This induces more effective tissue regeneration.

Furthermore, the PRP collected according to the present invention is injected in a mixture with a calcium chloride solution and type I collagen into all regions requiring bone defect treatment or wound healing, thereby achieving effective tissue regeneration.

Finally, as a result, the invention highly enhances the credibility of applying PRP to lesions and presents a good image to consumers.

BRIEF DESCRIPTION OF THE DRAWINGS

The foregoing and other objects, features and advantages of the present invention will become more apparent from the following detailed description when taken in conjunction with the accompanying drawings in which.

DETAILED DESCRIPTION OF THE INVENTION

Hereinafter, a preferred embodiment according to the present invention, for exhibiting these effects, will be described in detail with reference to accompanying drawings.

Figure 1:
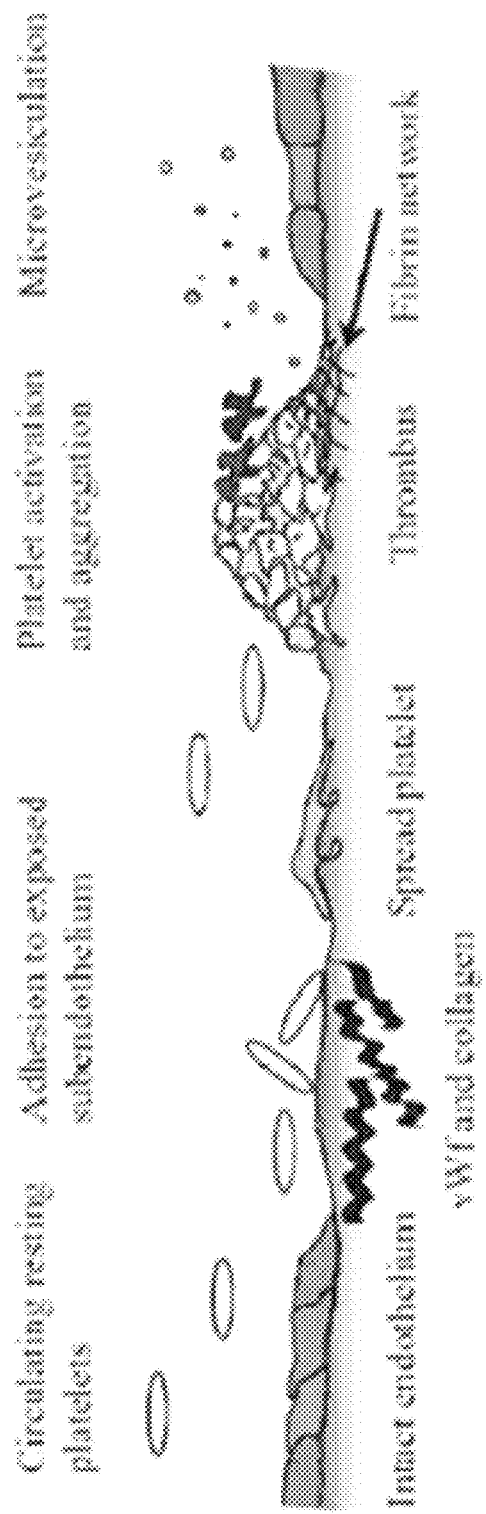
FIG. 1 is a view illustrating a model wherein adsorption and activation sequentially occur and aggregation is progressed through an interaction between platelets and subendothelial proteins.
Figure 2:
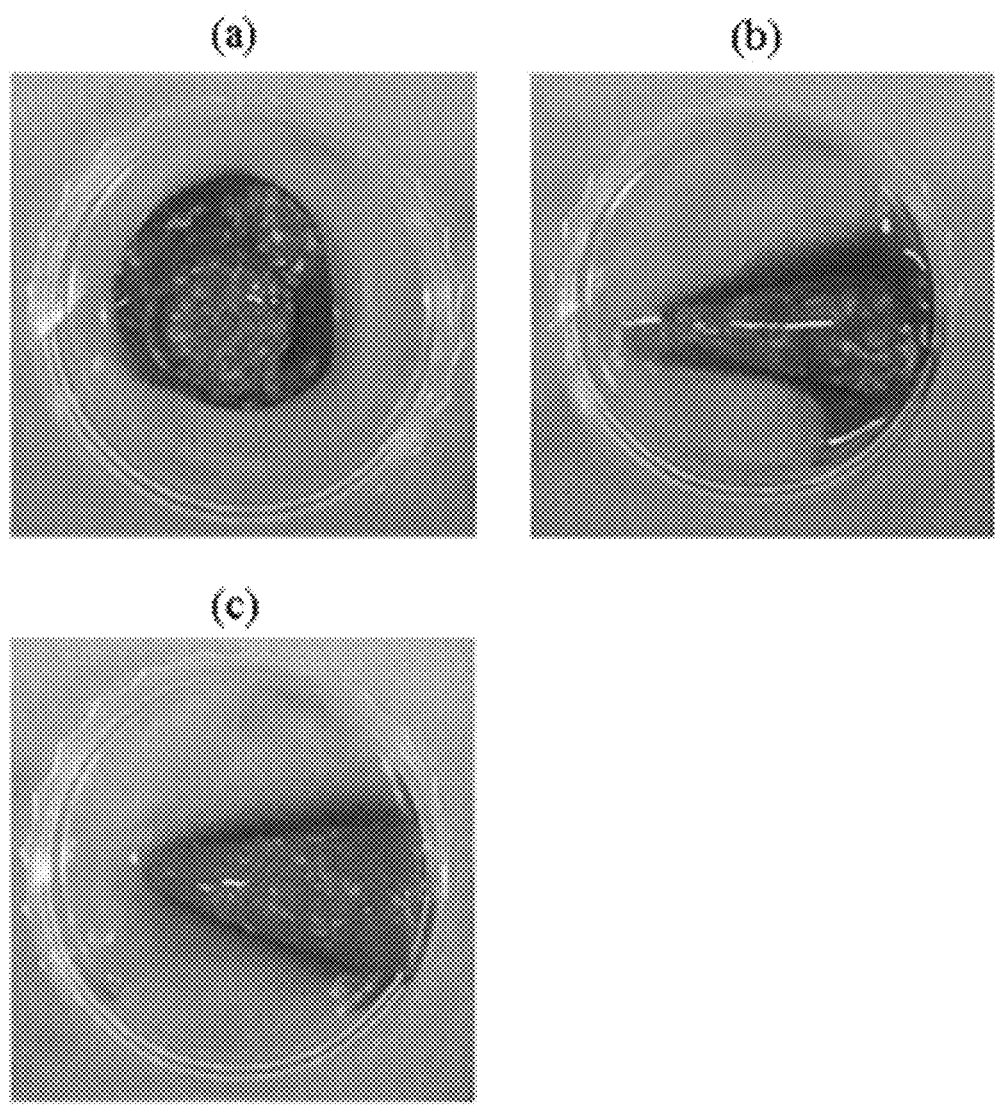
FIG. 2 shows photographs on 1 mL of platelet rich plasma (PRP) separated from whole blood in a mixture with a calcium chloride solution and type I collagen, in which in FIG. 2(a), the calcium chloride solution is included in an amount of 0.25 mg/mL, in FIG. 2(b), the calcium chloride solution is included in an amount of 0.3 mg/mL, and in FIG. 2(c), the calcium chloride solution is included in an amount of 0.5 mg/mL.
Figure 3:
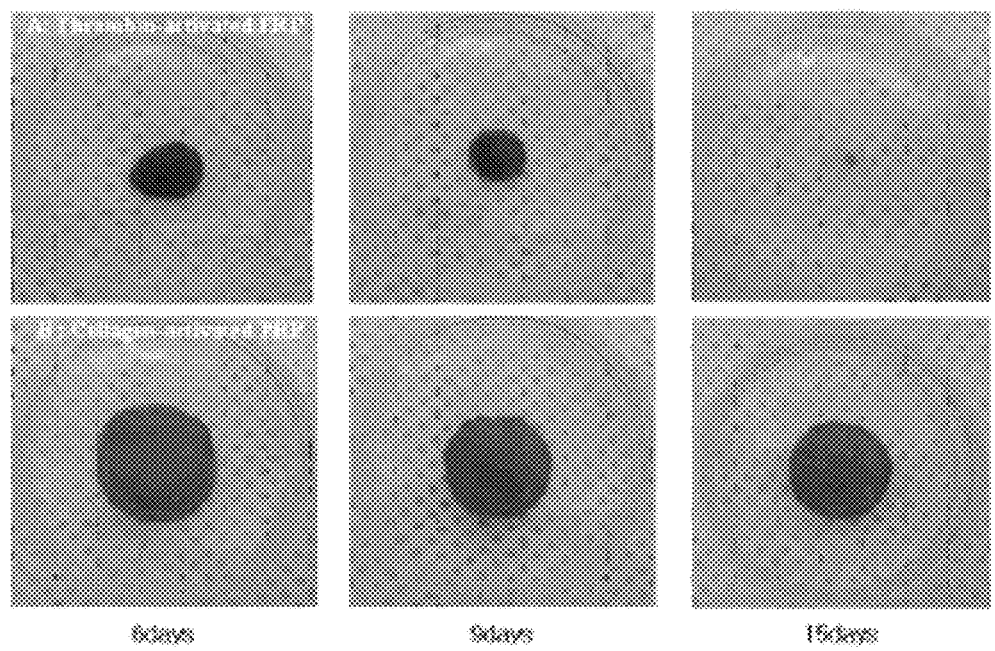
FIG. 3 shows photographs of the culture of a conventional thrombin mixture (A) and the inventive type I collagen mixture (B).

According to the present invention, a composition for inducing tissue regeneration by activating platelet rich plasma (PRP), and a method of manufacturing the same are configured as shown in FIGS. 2 and 3.

In the following descriptions of the present invention, a detailed description of known functions and configurations incorporated herein will be omitted when it is determined that the detailed description of the known functions and configurations may unnecessarily obscure the subject matter of the present invention.

Also, the terms described below are set in consideration of their functions in the invention, which may be varied according to a manufacturer' purpose or conventional use. Thus, their definitions may be based on the description of this specification.

First, in the present invention, a composition for inducing tissue regeneration by activating platelet rich plasma (PRP) is manufactured by the steps of: separating PRP from whole blood; mixing the PRP with a calcium chloride solution; and mixing the mixture of the PRP and the calcium chloride solution with type I collagen.

Meanwhile, in the present invention, the composition may be variously applied, and may be made in various forms.

Also, it should be understood that the present invention is not limited to specific embodiments mentioned in the detailed description, and include modifications, equivalents, and alternatives within the spirit and scope of the appended claims of the present invention.

Hereinafter, the operative effects of the inventive method of manufacturing the composition for inducing tissue regeneration by activating PRP, as configured above, will be described.

First, the inventive method includes the step of separating PRP from whole blood.

Herein, the step of separating PRP from the whole blood includes the step of collecting 10 ml of whole blood from an animal or a patient into a vacuum test tube containing 3.2% sodium citrate, and primarily centrifuging the whole blood (1,750~1,900 g) for 3 to 5 minutes.

Then, through the configuration, a supernatant liquid (plasma layer) including buffy coat is collected.

The collected supernatant liquid (plasma layer) including buffy coat is transferred to a new vacuum test tube by a blunt needle, and is secondarily centrifuged (4,500~5,000 g) for 4 to 6 minutes.

Then, the PRP concentrated in a bottom layer (from the bottom to the height of about 1 mL of the test tube) is collected by a blunt needle.

Also, the inventive method includes the step of mixing the PRP with a calcium chloride solution.

Herein, in the step of mixing the PRP with the calcium chloride solution, about 1 mL of PRP collected from the step of separating the PRP from the whole blood is mixed once with a calcium chloride solution with a concentration of 0.30~0.55 mg/mL by a Connecta.

Also, the inventive method includes the step of mixing the mixture of the PRP and the calcium chloride solution with type I collagen so as to manufacture the composition for inducing tissue regeneration by activating PRP.

Herein, the step of mixing the mixture of the PRP and the calcium chloride solution with type I collagen includes the step of leaving the type I collagen at room temperature.

Then, the mixture of the PRP and the calcium chloride solution is mixed with the opaque type I collagen with a concentration of 20~50 mg/mL four times through connection by a Connecta (three-way connector).

Next, the mixture of the PRP and the type I collagen mixture, charged in a syringe, is injected into all regions in need of tissue regeneration in cases such as bone defect treatment and wound healing.

The type I collagen preferably has a concentration of 20~50 mg/mL.

Furthermore, the type I collagen is preferably left at room temperature for 15 to 30 minutes.

Hereinafter, Examples of the present invention will be described.

Example 1

First, a kit for PRP separation is prepared as below.
1) A vacuum test tube containing 3.2% sodium citrate
2) A vacuum test tube holder
3) A vacuum test tube needle
4) A vacuum test tube (Plain type)
5) A 3 mL syringe
6) A blunt needle From the components as mentioned above, a PRP separation method can be deduced. First, 1) From a patient, 10 mL of whole blood is collected into a vacuum test tube containing 3.2% sodium citrate.

2) The whole blood charged in the vacuum test tube is centrifuged (1,750~1,900 g) for 3 to 5 minutes. Herein, the gravity acceleration and the time of the centrifugal separator are set to be optimum levels for separating the whole blood into hemocytes, buffy coat, and plasma.

3) After the cap of the vacuum test tube is opened, a supernatant liquid (plasma layer) including buffy coat is collected and transferred to a new vacuum test tube (plain type) by using a syringe provided with a blunt needle.

4) The plasma including buffy coat, transferred to the new vacuum test tube, is centrifuged (4,500~5,000 g) for 4 to 6 minutes. Herein, the gravity acceleration and the time of the centrifugal separator are set to be optimum levels for concentrating PRP within the plasma.

5) After the cap of the vacuum test tube is opened, the PRP concentrated in a bottom layer of the test tube (from the bottom to the height of about 1 mL of the test tube) is collected by using a syringe provided with a blunt needle.

6) In order to determine the separation efficiency of 1 mL of platelets separated from 10 mL of whole blood, a platelet-specific surface marker, that is, CD41, and a leukocyte-specific surface marker, that is, CD45 are reacted. Then, flow cytometry is used to measure the number of expressing cells. As a result, the number of platelets of the separated PRP is 5.8 to 7.6 times higher that than in the baseline. In the clinically required recommendations, the number is required to be 4.0 to 6.0 times (about 1,000,000 platelets/mL) higher than a baseline per volume of 6 mL of whole blood. Thus, the PRP separation method satisfies the recommendations. Also, the number of leukocytes is 2.8 to 4.2 higher than a baseline. Thus, in the application of the PRP, it is expected to achieve an antiviral effect.

Also, as noted in Table below, the whole blood is centrifuged ($1^{st}$: 1,750~1,900 g, 3 to 5 minutes, $2^{nd}$: 4,500~5,000 g, 4 to 6 minutes) twice so as to separate 1 mL of PRP. Then, a platelet-specific surface marker, that is, CD41, and a leukocyte-specific surface marker, that is, CD45 are reacted. Then, flow cytometry is used to measure the number of expressing cells. As a result, the number of platelets of the separated PRP is 5.8~7.6 higher than a baseline, and the number of Leukocytes is 2.8 to 4.2 higher than a baseline.

TABLE 1

| Sample | Platelet Count ($\times 10^8$/mL) | | Leukocytes ($\times 10^6$/mL) | |
|---|---|---|---|---|
| | Whole Blood Baseline | PRP (times baseline) | Whole Blood Baseline | PRP (times baseline) |
| Sample 1 | 2.46 | 14.81 (6.02) | 8.7 | 29.7 (3.41) |
| Sample 2 | 1.18 | 11.27 (6.20) | 4.3 | 14.9 (3.50) |
| Sample 3 | 2.11 | 15.24 (7.22) | 5.0 | 20.9 (4.18) |
| Sample 4 | 2.62 | 16.15 (6.16) | 12.1 | 39.3 (3.27) |
| Sample 5 | 1.94 | 11.58 (6.00) | 4.6 | 12.9 (2.80) |
| Sample 6 | 2.36 | 20.09 (5.81) | 6.2 | 25.2 (4.06) |
| Sample 7 | 2.55 | 17.48 (6.85) | 6.4 | 30.7 (4.80) |
| Sample 8 | 1.77 | 13.52 (7.64) | 4.8 | 17.9 (3.73) |
| Sample 9 | 2.13 | 15.6 (7.32) | 5.0 | 17.9 (3.58) |
| Average | 2.19 | 15.08 (6.88) | 6.3 | 23.3 (3.7) |

Example 2

A kit for transplanting a mixture of PRP, a calcium chloride solution, and type I collagen is prepared as below.
1) 1 mL, 3 mL syringes
2) A Connecta (three-way connector)
2) A calcium chloride solution
3) 20~50 mg/mL type I collagen From the components as mentioned above, a method of transplanting the mixture of the PRP, the calcium chloride solution, and the type I collagen can be deduced. First, 1) A syringe charged with 1 mL of PRP is connected to a syringe charged with a calcium chloride solution with a concentration of 0.30~0.55 mg/mL through a Connecta, and the materials are mixed once.

In other words, FIG. 2 shows photographs of 1 mL of PRP separated from whole blood in a mixture with a calcium chloride solution and type I collagen, in which in FIG. 2(a), the calcium chloride solution is included in an amount of 0.25 mg/mL, in FIG. 2(b), the calcium chloride solution is included in an amount of 0.3 mg/mL, and in FIG. 2(c), the calcium chloride solution is included in an amount of 0.5 mg/mL. In the present invention, for platelet aggregation of the mixture of the calcium chloride solution and the type I collagen, the optimum concentration of calcium chloride preferably ranges from 0.30 to 0.55 mg/mL.

A calcium ion ($Ca^{2+}$) as a component for a calcium chloride solution performs a role of converting solubility into insolubility in blood coagulation. Such a characteristic of the calcium ion ($Ca^{2+}$) induces platelet aggregation of the mixture of 1 mL of separated PRP and type I collagen. Then, if the concentration of the calcium chloride solution for platelet aggregation is 0.25 mg/mL or less, platelet aggregation is not formed. On the other hand, if the concentration is 0.55 mg/mL or more, cell damage is caused by osmotic pressure.

2) The type I collagen with a concentration of 20~50 mg/mL is left at room temperature for 15 to 30 minutes so as to change soluble collagen into fibrillar collagen. Herein, the reason the type I collagen is left at room temperature is as follows: first, the type I collagen is warmed so that the type I collagen in a soluble collagen state can be fibrillar-collagenated; second, there is hardly any difference in the amounts of released growth factors between the mixture of fibrillar-collagenated type I collagen with the PRP, and the mixture of type I collagen in a soluble collagen state with the PRP; and third, in general, fibrillar-collagenated type I collagen can more effectively induce platelet aggregation and support platelet adhesion than soluble collagen.

3) A syringe charged with the mixture of 1 mL of PRP and the calcium chloride solution is connected to the same amount of fibrillar type I collagen with a concentration of 20~50 mg/mL through a Connecta, and the materials are mixed with each other four times.

4) The mixture of the PRP, the calcium chloride solution and the type I collagen, charged in a syringe, is injected into all regions in need of tissue regeneration in cases such as bone defect treatment and wound healing.

Example 3

1) A mixture the PRP, a calcium chloride solution and type I collagen, charged in a syringe, is charged into a round-bottom glass tube.

2) The mixture is cultured in a 37° incubator for 15 minutes, and clotted. Herein, through the culturing of the mixture in the 37° incubator, it is possible to achieve the same condition as that where the mixture is transplanted into a tissue region and clotted.

3) The clotted mixture is placed in a sterilized 24-well culture vessel added with 1 mL of DMEM, and cultured in a 37° incubator.

Through the above described method, 10 mL of whole blood is collected from a patient and is subjected to two centrifugation steps to obtain 1 mL of concentrated PRP. The PRP is firstly mixed with a calcium chloride solution, and secondly mixed with type I collagen. Then, the mixture is transplanted into all regions in need of tissue regeneration in cases such as bone defect treatment and wound healing. In this method, there is no clinical rejection. Also, it is possible to separate PRP, mix with the PRP with type I collagen, and transplant the mixture, within a short time. Thus, it is possible to effectively and quickly induce tissue regeneration such as bone defect treatment and wound healing.

Especially, FIG. 3 shows cultures when separated PRP was activated with each of Thrombin and type I collagen, and a culture medium was cultured in a 5% $CO_2$ incubator (37° C.). After 15 days, most of a conventional thrombin mixture (A) was degraded. On the other hand, the inventive collagen mixture (B) maintained its initial shape with little change in size for 15 days.

In the inventive composition for inducing tissue regeneration by activating PRP, and the method of manufacturing the same, the technical spirit can be achieved in actuality through repetition with the same results. Especially, realization of the invention can facilitate technical development and contribute to industrial development. Thus, the invention deserves to be protected.

The invention claimed is:

1. A method of manufacturing a composition for inducing tissue regeneration by activating platelet rich plasma (PRP), the method comprising the steps of:
    separating the PRP from whole blood, wherein the separating step further comprises the steps of:
        collecting 10 ml of the whole blood from an animal or patient into a vacuum test tube containing 3.2% sodium citrate, and primarily centrifuging the collected whole blood at 1,750-1,900 g for 3 to 5 minutes;
        collecting a supernatant liquid comprising a plasma layer with a buffy coat obtained from said centrifugation;
        transferring the collected supernatant liquid to a new vacuum test tube by a blunt needle, and secondarily centrifuging the collected supernatant liquid at 4,500-5,000 g for 4 to 6 minutes; and
        collecting the PRP concentrated in a bottom layer by another blunt needle;
    mixing 1 mL of the PRP collected from the separating step with a calcium chloride solution with a concentration of 0.30-0.55 mg/mL by a three-way connector; and
    mixing a mixture of the PRP and the calcium chloride solution with type I collagen, wherein the mixing step of mixing the mixture of the PRP and the calcium chloride solution with the type I collagen further comprises the steps of:
        leaving the type I collagen at a room temperature for 15 to 30 minutes before mixing; and
        mixing the mixture of the PRP and the calcium chloride solution with the type I collagen with a concentration of 20-50 mg/mL, in an opaque phase, four times by another three-way connector.

2. The method of claim 1, further comprising the step of:
    injecting the mixture of the PRP, the calcium chloride solution and the type I collagen, charged in a syringe, into all regions in need of the tissue regeneration.

* * * * *